United States Patent [19]
Langer et al.

[11] Patent Number: 5,808,157
[45] Date of Patent: Sep. 15, 1998

[54] PROCESS FOR PRODUCING AROMATIC AMINES

[75] Inventors: Reinhard Langer; Hans-Josef Buysch, both of Krefeld; Paul Wagner, Düsseldorf; Ursula Pentling, Kempen, all of Germany

[73] Assignee: Bayer Aktiengesellschaft, Leverkusen, Germany

[21] Appl. No.: 511,165

[22] Filed: Aug. 4, 1995

[30] Foreign Application Priority Data

Aug. 8, 1994 [DE] Germany ............... 44 28 017.3

[51] Int. Cl.$^6$ .................................. C07C 209/04
[52] U.S. Cl. .................. 564/422; 564/410; 564/420
[58] Field of Search ............. 564/416, 420, 564/422

[56] References Cited

U.S. PATENT DOCUMENTS

| | | | |
|---|---|---|---|
| 3,136,818 | 6/1964 | Sperber et al. | 260/580 |
| 3,636,152 | 1/1972 | Szigeth | 260/580 |
| 3,871,445 | 3/1975 | Wanka et al. | 165/107 |
| 4,265,834 | 5/1981 | Birkenstock et al. | 564/421 |
| 4,732,918 | 3/1988 | Lohmueller et al. | 518/712 |
| 4,740,621 | 4/1988 | Adams et al. | 564/419 |

FOREIGN PATENT DOCUMENTS

| | | |
|---|---|---|
| 1452466 | 10/1976 | United Kingdom . |
| 2182330 | 5/1987 | United Kingdom . |

OTHER PUBLICATIONS

Gramatikov et al., "Adiabatic process of catalytic reduction of nitrobenzene to aniline", Izv. Khim. vol. 16(1–2), 38–43, 1983.

Chemical Abstracts, vol. 112, No. 4, Jan. 22, 1990, Abstract No. 26341t, Seite 362, Sparite 2, & CS-A-258 375 (Pavlas, Pavel et al) Apr. 14, 1989.

Chemical Abstracts, vol. 100, No. 16, Apr. 16, 1984, Abstract No. 123155v, Gramatikov, K. et al, 'Adiabatic process of catalytic reduction of nitrobenzene to aniline.' Seite 108, Spalte 2: & Izv. Kim, Bd. 16, No. 1–2, 1983, Seiten 38–43.

Chemical Abstracts, vol. 117, No. 20, Nov. 16, 1992, Abstract No. 194013j, Seite 120, Spalte 2, & CS-A-263 430 (Rozinek, Radovan et al) Jan. 20, 1992.

Hydrocarbon Processing 59 (Nov. 1979, No. 1, p. 136).

Ullmanns Encyclopedia of Industrial Chemistry (Fifth, Completely Revised Edition, vol. B4, pp. 95–102, and pp. 210–216).

*Primary Examiner*—Allen J. Robinson
*Assistant Examiner*—Barbara Badio
*Attorney, Agent, or Firm*—Joseph C. Gil; Lyndanne M. Whalen

[57] ABSTRACT

Aromatic amines are produced by hydrogenation of the associated aromatic nitro compounds in the gas phase over fixed catalysts. The catalysts contain active hydrogenation metals on supports. The reaction is conducted at a pressure of 2–50 bar and at a temperature in the range 250°–500° C. under adiabatic conditions. A circulating gas is passed over the catalyst, which circulating gas contains 3–150 moles of hydrogen, 2–100 moles of the amino groups to be formed per mole of nitro groups, and 2 to 6 moles of water per amino group equivalent. The amine and water formed, as well as a purification stream, are separated from the circulating gas. Thereafter the circulating gas is enriched with volatilised aromatic nitro compound and fresh hydrogen and recycled.

10 Claims, No Drawings

PROCESS FOR PRODUCING AROMATIC AMINES

This invention relates to a process for the hydrogenation of aromatic nitro compounds to form amines in the gas phase on fixed catalysts, wherein heat is neither externally supplied to nor externally extracted from the catalyst, i.e. the process is carried out adiabatically, and wherein the aromatic nitro compound to be reacted is passed over the catalyst under pressure with an abundance of the aromatic amine produced from it and an abundance of water and hydrogen.

Aromatic amines are important intermediates which have to be available at low cost and in large amounts. Installations with very large capacities therefore have to be constructed for the hydrogenation of nitrobenzene, for example.

The hydrogenation of aromatic nitro compounds is a strongly exothermic reaction. Thus at 200° C. about 488 kJ/mole (117 kcal/mole) are released during the hydrogenation of nitroxylene to form xylidine, and about 544 kJ/mole (130 kcal/mole) are released on the hydrogenation of nitrobenzene.

The dissipation and utilisation of the heat of reaction is accordingly an important consideration when carrying out processes for the hydrogenation of aromatic nitro compounds.

Thus in one established procedure the catalyst is operated as a fluidised, thermally stabilised bed (U.S. Pat. No. 3,136,818). Problems arise in the effective dissipation of heat from this procedure due to a non-uniform residence time distribution (nitrobenzene breakthrough) and attrition of the catalyst.

Narrow residence time distributions and low catalyst attrition are possible in reactors containing fixed catalyst beds. Problems arise in such reactors, however, which are associated with keeping the temperature of the catalyst beds constant. In general, thermostatted tube bundle reactors are used, which have a very expensive cooling circuit, particularly for large reactors (DE-OS 2 201 528, DE-OS 3 414 714). Reactors of this type are complex, and result in high capital costs. Problems as regards mechanical strength and achieving uniform constancy of temperature of the catalyst bed, which increase rapidly with increasing reactor size, make large installations of this type uneconomic.

Simple reactors such as those employed for the process according to the invention, which is described in detail below, contain catalyst beds only and have no system for controlling the heat balance in the reactor. They can easily be scaled up to an industrial scale, and are economic and robust in all sizes. In this type of reactor the enthalpy of reaction is quantitatively reflected in the temperature difference between the educt and product gas streams. Hitherto, the use of reactors such as these for the strongly exothermic hydrogenation of aromatic nitro compounds has not been described; nor have suitable catalysts and suitable modes of operation been demonstrated.

GB 1,452,466 relates to a process for the hydrogenation of nitrobenzene, in which an adiabatic reactor is disposed downstream of an isothermal reactor. In this process the major part of the nitrobenzene is reacted in a thermostatted tube bundle reactor, and it is only the hydrogenation of the residual content of nitrobenzene which is effected, using a relatively slight excess of hydrogen (less than 30:1), in an adiabatic reactor.

The advantage of completely dispensing with a thermostatted reactor, by conducting the reaction purely adiabatically, was not recognised.

DE-AS 1 809 711 is concerned with the uniform introduction of liquid nitro compounds into a hot gas stream by spraying, preferably at constricted points directly upstream of the reactor. The construction of the reactor is not discussed in the text of this Application. However, it can be inferred from the Example that despite a considerable excess of hydrogen at least 34% of the enthalpy of reaction does not leave the reactor with the product gas.

DE-OS 36 36 984 describes a process for doubling the production of aromatic nitro and dinitro compounds from the corresponding hydrocarbons by nitration and subsequent hydrogenation. Hydrogenation is carried out in the gas phase at temperatures between 176° and 343.5° C. It can be inferred from the Example that the hydrogen stream also serves to dissipate the heat of reaction from the reactors. An apparatus for gas phase hydrogenation is described which essentially consists of two reactors connected in series, with intermediate cooling and the intermediate supply of educt. The size and construction of the reactors are not discussed. However, from the temperature profile of the reactors it can be inferred that a not inconsiderable proportion of the heat of reaction does not leave the reactor with the product gas stream. Thus reactor No. 1 has an inlet temperature of 181.7° C., a hottest point of 315.6° C. and an outlet temperature of 277.2° C. Reactor No. 2 has an inlet temperature of 203.9° C., a hottest point of 300° C. and an outlet temperature of 296.7° C. DE-OS 36 36 984 does not state whether the reactors require a cooling device or not when the reaction is performed on an industrial scale, of the order of 80,000 tonnes per annum for example. Neither in DE-OS 36 36 984 nor in DE-OS 18 09 711 is there any explicit discussion of the problem of heat dissipation in gas phase hydrogenation reactions.

The fact that new improved installations for the hydrogenation of nitrobenzene to produce aniline have been put into operation can be inferred from the journal "Hydrocarbon Processing 59" (Volume 59, 1979, number 11, page 136). It can be inferred from this publication that in these new installations the recovery of steam and the reaction are effected as closely coupled operations in one process step.

In all the above publications Cu catalysts are used which are exclusively operated at low loadings (<0.1 g (nitrobenzene)/ml (catalyst)-h) and at low temperatures. This results in low space-time yields.

In addition to the aforementioned copper catalysts, numerous other contact catalysts for the gas phase hydrogenation of aromatic nitro compounds have been described. These have been described in many publications and comprise Pd, Pt, Ru, Fe, Co, Ni, Mn, Re, Cr, Mo, V, Pb, Ti, Sn, Dy, Zn, Cd, Ba, Cu, Ag or Au as the active hydrogenation elements and compounds, in part as oxides, sulphides or selenides and also in the form of a Raney alloy, as well as on supports such as $Al_2O_3$, $Fe_2O_3/Al_2O_3$, $SiO_2$, silicates, carbon, $TiO_2$ or $Cr_2O_3$.

These catalysts are also operated only at low loadings, and in a temperature range below 350° C.

In none of the prior publications is it stated that it is advantageous to pass a larger amount of aromatic amine and water over the contact catalyst with the aromatic nitro compound.

On the contrary, pure hydrogen is mostly passed over the catalyst with the pure nitro compound. In DE 1 809 711 and DE 3 636 984 there are amounts of aromatic amine in the educt for the reactor which are relatively small compared with the amount of nitro compound supplied, however. In DE 1 809 711 about 1502 g of hydrogen are fed into the reactor per 1000 g of nitrobenzene, but only 692 g of water and only 92.9 g of aniline are fed in. This merely reflects the fact that water and aniline can only be removed incompletely from the circulating gas at reasonable cost.

It can be stated that, according to the prior art, the gas phase hydrogenation of aromatic nitro compounds has always been conducted based on the following principle: vaporisation of the aromatic nitro compound, passing the aromatic nitro compound over a catalyst with an excess of hydrogen, separating the aromatic amine and water produced as completely as possible from the excess hydrogen, and recycling the excess hydrogen.

It has surprisingly been found that a particularly favourable procedure for the gas phase hydrogenation of aromatic nitro compounds is achieved, which enables aromatic amines to be produced using simple apparatus, at high energy yields and with high product selectivities, if large amounts of aromatic amine and water are recycled with the circulating hydrogen, and if principally only the water of reaction and the aromatic amine are separated from this gas circuit.

The present invention relates to a process for producing aromatic amines of formula

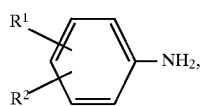

where
R$^1$ and R$^2$ represent hydrogen, methyl or ethyl, independently of each other, and R$^1$ may in addition represent amino,
by the hydrogenation of aromatic nitro compounds of formula

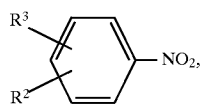

where
R$^2$ and R$^3$ represent hydrogen, methyl or ethyl, independently of each other, and R$^3$ may in addition represent nitro,
in the gas phase with H$_2$ on fixed catalysts, which is characterised in that it is operated at a pressure of 2 to 50 bar, preferably 3–20 bar, most preferably 4–10 bar, and at a temperature in the range 250°–500° C., preferably 290°–470° C., more preferably 320°–440° C., most preferably 340°–410° C., under adiabatic conditions, wherein a circulating gas flows over the catalyst, which circulating gas contains 3–150 moles of hydrogen, 2–100 moles of aromatic amino groups per mole of nitro groups and 2–6 moles, preferably 2.1–4 moles, most preferably 2.2–3 moles, of water per mole of amino groups, the amount of amine and water formed per unit time is condensed out, and the residual circulating gas, optionally after the separation of a purification stream, is recycled, and is enriched with vaporised aromatic nitro compound and with fresh hydrogen.

The nitro groups are found exclusively in the educt molecules, and the aromatic amino groups are found exclusively in the product molecules.

Aromatic nitro compounds of formula

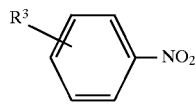

are preferably used, where
R$^3$ represents hydrogen, methyl or ethyl.
Nitrobenzene is most preferably used.

A product installation according to the invention consists of at least one adiabatic reactor containing a fixed catalyst. A maximum of 10, preferably a maximum of 5, most preferably a maximum of 3 such reactors are connected in series. Each reactor connected in series may be replaced by a plurality of reactors connected in parallel. A maximum of 5, preferably a maximum of 3, most preferably a maximum of 2 reactors are connected in parallel as a replacement for one reactor. The process according to the invention may accordingly comprise a maximum of 50 reactors and a minimum of one reactor.

A larger number of reactors containing one catalyst bed may be replaced by a smaller number containing a plurality of catalyst beds.

The reactors consist of simple vessels containing insulated catalyst beds, as described, for example, in Ullmanns Encyclopedia of Industrial Chemistry (Fifth, Completely Revised Edition, Vol. B4, pages 95–102, pages 210–216).

The catalyst beds are installed according to the prior art or between gas-permeable walls. For shallow beds in particular, engineering devices for achieving uniform gas distribution are provided above, below or above and below the bed. These may be perforated plates, bubble trays, valve trays or other inserts which result in a uniform entry of the gas into the catalyst bed by the production of a small but uniform pressure drop. Metal or ceramic sintered plates are preferably used, e.g. those sold by the Krebsöge company.

Instead of catalyst beds, suitable packings may also be used as the support material. These may be honeycomb bodies or corrugated sheets, such as those marketed by the Sulzer company under the trade name Katapak, for example. For their use according to the invention, these packings are of course made active by the deposition of suitable metal compounds before they are introduced into the reactor.

Upstream of each catalyst bed, fresh aromatic nitro compound is injected into the circulating gas stream, which mainly consists of recycled and freshly added hydrogen and of recycled aromatic amine and water. This may be effected as described in DE 1 809 711, but the aromatic nitro compound is preferably completely volatilised in the fresh hydrogen and then introduced into the gas stream in gaseous form. The advantage of this mode of operation is the significantly reduced formation of deposits in the reactor and in the feed lines. Vaporisation may be effected according to the prior art in known evaporators, such as falling film, inclined tube, injection, thin film, recirculating or helical coil evaporators, for example. Volatilisation is preferably effected in falling film and injection evaporators, most preferably in falling film evaporators. In addition, it is possible to spray the liquid aromatic nitro compound into the fresh hydrogen stream or circulating gas hydrogen stream by means of single-fluid or two-fluid nozzles, wherein recombination of the educt gas stream can be effected after superheating in a heat exchanger. A droplet separation stage which is known in principle may be connected downstream of the volatilisation stage. The educt gas stream is admixed with the circulating gas stream in the known manner by means of an appropriate feeding and distribution system, or by means of mixing devices, such as the Type SUX or SMV mixers manufactured by Sulzer or Kenics, for example.

After each catalyst bed the product gas leaving it can be cooled with the generation of steam. For this purpose it is passed through one or more heat exchangers. These may be the heat exchangers known to one skilled in the art, such as tube bundle, plate, annular channel, spiral flow or ribbed tube heat exchangers, for example.

After leaving each heat exchanger for the conversion of the heat of reaction into steam, a partial stream of the circulating gas may be branched off and cooled further in order to separate out the aromatic amine and the water formed. In a preferred and particularly economical manner this is preferably effected after the circulating gas has left the last heat exchanger.

The circulating gas stream subsequently passes through a compressor in order to compensate for the resistance to flow of the reactors and heat exchangers and to control the mass flow of the circulating gas.

The compressors may be simple, known apparatuses (e.g. blowers), since the pressure drop can be maintained at a low level by the mode of construction of the reactors. Dry-running radial or axial compressors are preferably used.

In principle, the circulating hydrogen which is removed from the circuit can be re-injected into the circulating gas stream at any point and recycled with it, just as the aromatic amine and the water of reaction can be removed from the circuit together with hydrogen at any point upstream of an aromatic nitro compound feed point and downstream of a reactor. The procedure is preferably as stated above, however.

In one particular embodiment the hydrogen removed from the circuit, which has been substantially freed from aromatic amine and water of reaction, is reintroduced (recycled) into the circulating gas stream upstream of the first reactor.

The gas stream upstream of each catalyst bed is as homogeneous as possible and contains 2 to 100 moles of aromatic amino groups, preferably 2.5 to 50 aromatic amino groups, more preferably 3 to 20 moles of aromatic amino groups, most preferably 3.5 to 10 moles of aromatic amino groups, per mole of nitro groups.

The circulating gas stream contains 2 to 6 equivalent moles of water, preferably 2.1 to 4 moles of water, most preferably 2.2 to 3 moles of water, per mole of amino groups.

The gas stream upstream of each catalyst bed contains 3–150 moles of hydrogen, preferably 6–125 moles of hydrogen, more preferably 12–100 moles of hydrogen, most preferably 25–75 moles of hydrogen, per mole of nitro groups.

The circulating gas is under pressure. The absolute pressure of the circulating gases is 2 to 50 bar, preferably 3–20 bar, most preferably 4–10 bar.

The temperature of the circulating gas is within the range from 250° to 500° C., preferably 290°–480° C., more preferably 320°–440° C., most preferably 340°–410° C. The temperature increases during the passage through the reactor as a result of the adiabatic method of operation.

The gas stream which is removed from the circuit for the separation of the aromatic amine and water of reaction formed is cooled to a temperature between 80° and 20° C., preferably 60°–25° C., most preferably 40°–30° C.

The condensate is passed into an engineering device for the separation of liquid phases, and the aqueous and organic phases are worked up separately.

The aromatic amine extracted from the aqueous phase is fed to the work-up stage for the organic phase. Work-up is effected in the known manner by distillation or by stripping with steam.

A certain amount of the hydrogen removed from the circulating gas is separated for the removal of gaseous impurities. The remainder is reheated, compressed and recycled to the circulating gas stream. This recycling stage may optionally be omitted.

The depth of the catalyst beds may be between 1 cm and 5 m, preferably between 5 cm and 2 m, more preferably between 10 cm and 1 m, most preferably between 30 cm and 60 cm.

All the contact catalysts described hitherto for the gas phase hydrogenation of nitro compounds can be used. These contain the elements of what are termed the auxiliary groups of the Periodic Table of the Elements, either as metals or alloys or as mixed oxides, and optionally on an inert support material.

Suitable support materials include: $\alpha$- and $\gamma$-$Al_2O_3$, $SiO_2$, $TiO_2$, lateritic soil and limonite, $Fe_2O_3/Al_2O_3$ mixtures, $CuO/Cr_2O_3$ mixtures, waterglass, graphite, activated carbon (BET specific surface 20–100 $m^2/g$) and carbon fibres. Other supports may also be used in principle, however.

The catalysts according to DE 2 849 002 are preferably used. These are supported catalysts on inert supports with a BET specific surface less than 20 $m^2/g$, or on $Al_2O_3$ with a BET specific surface less than 10 $m^2/g$. The pretreatment with a base which is described in DE-OS 2 849 002 is not absolutely necessary.

Three classes of active materials are deposited on the support material:

(a) 1–100 g/l of a catalyst comprising one or more metals of Groups VIIIa, Ib and IIb of the (Mendeleev) Periodic Table of the Elements, (b) 1–100 g/l of one or more transition metals of Groups IIb, IVa, Va and VIa, and (c) 1–100 g/l of one or more main group elements of Groups IVb and Vb.

Elements of Group IIb can thus act as active materials (a) and (b). Preferred active materials comprise Pd as metal (a), V, Nb, Ta, Cr, Mo, W or Ti as transition metal (b), and Pb and Bi as main group element (c).

The following are most preferably deposited on the support:

(a) 20 to 60 g Pd, (b) 20 to 60 g V, and (c) 10 to 40 g Pb.

The active materials are deposited on the support in the form of their soluble salts. A plurality of treatments (impregnations) per component may be necessary. The active materials are preferably merely deposited in the form of a skin, i.e. in the vicinity of the surface of the catalyst.

These contact catalysts are operated in a temperature range which is between the input temperature of the educt gas and a maximum of 500° C., preferably a maximum of 480° C., more preferably a maximum of 460° C., most preferably a maximum of 440° C.

For the process according to the invention, the metal content of these catalysts may be considerably higher than that described in DE 2 849 002. In this respect, catalysts having a high content of noble metals exhibit surprisingly high selectivities. Per 1000 ml of support material, the content of Pd in these contact catalysts is a minimum of 1 g and a maximum of 100 g, preferably 60 g, more preferably 40 g, and most preferably 20 g. V and Pb may be deposited with their contents increased accordingly.

Other preferred catalysts are those which contain only Pd, or Pd with Rh and/or Ir and or Ru on carbon supports having low BET specific surfaces. Support materials such as these contain graphite, and include graphite itself and cokes such as needle coke or petroleum coke. These supports have a BET specific surface of 0.2–10 $m^2/g$. Catalysts are used according to the invention which contain 0.001–1.5 weight % Pd, based on the total weight of catalyst, on graphite or graphite-containing coke as the support, wherein 0–40 relative percent of the amount of Pd may be replaced by Ir and/or Rh and/or Ru. These catalysts may therefore contain noble metal(s) in the following arrangements on the support:

Pd only, Pd/Ir, Pd/Rh, Pd/Ru, Pd/Ir/Rh, Pd/Ir/Ru, Pd/Rh/Ru or Pd/Ir/Rh/Ru. One of the cited combinations of two noble metals or Pd on its own are used in many cases. The palladium is preferably present in the catalysts on carbon supports in an amount of 0.005–1 weight %, preferably 0.05–0.5 weight %, based on the total weight of catalyst. The lower limit of zero for the relative percentages of the other cited platinum group metals indicates the use of Pd on its own. If the other platinum group metals are used, their content preferably amounts to 10–40 relative percent; amongst them, the weight ratio between each two of them is 1:1–3:1.

It has also proved to be advantageous if the aforementioned catalysts are doped in addition with compounds containing sulphur or phosphorus, preferably containing phosphorus. This additional content of dopant is 0.1–2 weight %, preferably 0.1–1 weight %, of sulphur or phosphorus, preferably phosphorus, in chemically bound form, based on the total weight of catalyst. Preferred phosphorus-containing compounds for doping the catalysts according to the invention include: phosphorus oxyacids $H_3PO_4$, $H_3PO_3$ and $H_3PO_2$, or their alkali salts, such as sodium dihydrogen phosphate, sodium or potassium phosphate or sodium hypophosphite for example.

The procedure for preparing the catalysts on carbon supports may be such that the said noble metals in the form of suitable salts, and the compound containing sulphur or phosphorus, are deposited on one of the said supports in the form of pellets, spheres, granulated extruded material or fragments of dimensions about 1–10 mm, drying being effected after deposition. Drying is effected in the known manner, for example at 100°–140° C. under a pressure ranging from reduced pressure to normal pressure, for example 1–1000 mbar; water pump pressure may be used as the reduced pressure, for example. Aqueous solutions may be used for the impregnation of the support. This is preferably the case for the compounds containing sulphur or phosphorus, water-soluble compounds of which are preferred. However, the noble metal salts are preferably dissolved and deposited in organic solvents, such as simple alcohols, ketones, cyclic ethers or nitriles. Examples of organic solvents such as these include methanol, ethanol, propanol, isopropanol, acetone, methyl ethyl ketone, dioxane, acetonitrile and comparable solvents. Methylene chloride and comparable solvents may also be used for salts containing organic anions. Examples of suitable salts of the noble metals include their chlorides, nitrates or acetates.

After impregnation and subsequent drying, the catalyst is available for use. It is preferably activated in the reactor by treatment with hydrogen at elevated temperature before the commencement of the hydrogenation of nitrobenzene. An elevated temperature such as this is within the range from 200°–400° C., for example, preferably from 230°–370° C.

The aforementioned catalysts are outstandingly suitable for use in the hydrogenation of nitrobenzene to form aniline.

If there is a decrease in the activity of the catalyst used, it can easily be regenerated in situ, i.e. in the hydrogenation reactor. For this purpose the catalyst is treated in succession at 350°–400° C. with steam, a nitrogen/air mixture or atmospheric air, and finally with nitrogen. Treatment with steam may be effected for 1 to 3 hours; treatment with air or with the nitrogen/air mixture may be effected for 1 to 4 hours. A regeneration step such as this is not possible for noble metal catalysts on supports other than the carbon supports described above, e.g. when using activated carbon as the support, since activated carbon starts to burn during a regeneration step such as this. Subsequent treatment with hydrogen at 200°–400° C. may be employed for re-activation of the catalyst.

These catalysts are operated in a temperature range below 480° C., preferably below 460° C., most preferably below 440° C.

The contact catalysts which have been described as those which are most preferred permit a particularly long period of operation between regenerations.

In principle, the catalyst grains may be of any shape, such as spheres, small rods, Raschig rings or granular materials or pellets. Shaped bodies are preferably used which result in catalyst beds having a low resistance to flow and good gas-surface contact, such as Raschig rings, saddles, cart wheels and spirals.

The process according to the invention enables gas phase hydrogenation to be effected particularly advantageously, resulting in constant, high selectivities for the aromatic amine and long catalyst service lifetimes between catalyst regeneration stages, which generally consist of burning off deposits rich in carbon.

One mode of procedure consists of operating at constant pressure, and of starting the catalyst at a particularly high loading. The loading is then decreased as deactivation of the catalyst takes place during period of operation between two regenerations, so that there is no breakthrough of aromatic nitro compound.

Another equivalent method consists of keeping the catalyst loading constant and starting with a low system pressure. The system pressure is slowly increased shortly before the aromatic nitro compound begins to break through.

A mode of operation may also be selected which lies between the extremes of constant pressure and constant loading. Starting is preferably effected under low pressure and low loading, both these variables then being increased during the deactivation of the catalyst.

In the process according to the invention the loading of the catalysts may be very high, and may amount to 0.1 g to 20 g of aromatic nitro compound per ml of catalyst per hour, preferably up to 15 g/ml.hour, more preferably up to 10 g/ml.hour, most preferably up to 5 g/ml.hour.

The process according to the invention is accordingly characterised by high space-time yields, which are associated with a reduction in size of the apparatus. Moreover, the process according to the invention enables standard apparatus to be used and enables high installation capacities to be obtained at low capital cost.

The gas circuit for dissipating the heat of reaction from the catalyst into the steam generator does not pass through any parts of the apparatus for separating out the reaction products, and accordingly does not have to be cooled to such an extent that the reaction product condenses out. Due to this feature, only small heat exchanger surfaces are required. Components and pipelines which have to cope with the large flow of circulating gas are restricted to the reactors, the high-temperature heat exchangers and the compressor.

The installation can be operated with a low pressure drop and thus with a large throughput of circulating gas, and therefore with a small temperature rise in the catalyst bed. This results in the capacity of recovering the heat of reaction at a high thermal level, which permits the profitable generation of high-pressure steam for power generation.

This leads to a perceptible improvement in the economics of the process.

The high temperatures, together with the dilution of the aromatic nitro compound with the aromatic amine, water and hydrogen, and the mode of operation involving a pressure gradient or pressure-loading gradient, result in an astonishingly high degree of selectivity over the entire production cycle between two catalyst regeneration stages by burn-off.

The process is particularly suitable for the conversion of nitrobenzene to aniline. In this respect, aniline is formed at a constant, high selectivity. This is obviously due to the fact that the ratio of nitro groups to aromatic amino groups is not higher than 0.5 in any catalyst volume.

EXAMPLE 1

400 g of EG 17 graphite granules manufactured by Ringsdorf (1–3 mm granules, tap density 650–1000 g/l, BET specific surface=0.3–0.4 $m^2/g$), with an absorption capacity of 7 ml acetonitrile per 100 g support were placed in a rotatable vessel and a solution of 1.66 g palladium(II) acetate in 26 g of acetonitrile was added. The mixture was rotated until the support material had completely absorbed the solution. This was followed by drying the solid for 5 minutes in a strong current of rising air at 40° C. Impregnation with palladium acetate in acetonitrile and subsequent drying was repeated again twice. The dried catalyst was then reduced in a stream of hydrogen at 100° C. for 3 hours.

EXAMPLE 2

5000 ml $\alpha$-$Al_2O_3$ manufactured by Condea ($\alpha$-alumina, density 1.02 g/ml, spheres with a diameter of 1 mm, BET specific surface=4 $m^2/g$) with an absorption capacity of 33.4 ml water per 100 g support, were placed in a rotatable vessel and a solution of 553 g disodium tetrachloropalladate in 1200 g water was added. The mixture was mixed by rotation until the whole of the solution had been absorbed by the support material. This was followed by drying the solid for 10 minutes in a strong current of rising air at 40° C. The dried catalyst was reduced with hydrogen for 3 hours at 350° C., the reduced, dried solid was then added at room temperature to a solution of 500 g oxalic acid dihydrate and 178.6 g vanadium pentoxide in 1030 g water, and was mixed by rotation until the whole of the solution had been absorbed by the support material. This was followed by drying the solid for 10 minutes in a strong current of rising air at 40° C., and thereafter by a repeated impregnation with the same amount of a vanadium oxalate solution, with subsequent drying in the warm air current. The dried catalyst was annealed for 4 hours at 300° C. and was then cooled to room temperature. This was followed by impregnation of the solid as described above with a solution of 128.2 g of lead(II) acetate trihydrate in 1200 g water. Thereafter the solid was again dried for 10 minutes in a strong current of rising air at 40° C., the dried catalyst was reduced for 3 hours at 350° C. with hydrogen, and was then washed with distilled water at room temperature until the wash water had a pH of 7. The catalyst obtained in this manner was dried for 10 minutes in a strong current of rising air at 40° C.

EXAMPLE 3

30 ml (31 g) of the catalyst prepared in Example 1 were introduced into a pressure-tight apparatus, consisting of three oil-heated evaporator superheaters, an insulated reaction tube fitted with electric trace heating, a condenser, a receiver vessel for the liquid product with automatic, level-controlled discharge, and a droplet separator.

The inside diameter of the reaction tube was 14.9 mm and its wall thickness was 3.2 mm. The reaction tube was provided from top to bottom, over a length of 300 mm in the direction of flow, with good heat transfer to the electric trace heating by means of copper cores (inside diameter=24 mm, outside diameter=44 mm), and was provided in the catalyst region below this with poor heat transfer to the electric trace heating over a length of 500 mm by means of an insulating tape 100 mm thick.

The space above the catalyst bed was provided over a length of 180 mm along the axis of the tube with a hollow metal tube (outside diameter=4 mm) for housing a thermocouple. Beds of 3 mm wire mesh were located above and below the catalyst bed for the fixation of the catalyst bed.

The apparatus was uniformly impinged upon by a constant flow of hydrogen at a defined pressure from the three evaporator superheaters. Water, aniline and nitrobenzene were pumped separately into the evaporators via metering pumps.

After complete volatilisation in the stream of hydrogen the "circulating gas stream" educts were combined and passed over the contact catalyst.

Operation of the installation was started by introducing 460 Nl (Normliter) of hydrogen at 4 bar, heating the oil-thermostatted evaporator superheaters to 300° C. and heating the reaction tube containing the catalyst to 320° C.

After the desired temperatures had been reached the aniline addition rate was adjusted to 182 g (2 moles) per hour and the water addition rate was adjusted to 36 g (2 moles) per hour.

Thereafter, feeding was commenced of 32.6 g (0.27 moles) of nitrobenzene per hour into the third evaporator.

The catalyst temperature, which had previously been a uniform 320° C. along the axis of the tube, increased rapidly to about 439° C. with the commencement of feeding of the nitrobenzene.

The liquid product mixture consisted of an aqueous phase and an organic phase. The organic phase contained 98.5% aniline, contaminated with 0.5% cyclohexylaniline and 0.6% diphenylamine, and was recycled as "aniline" at 182 g per hour to the aniline evaporator.

The aqueous phase consisted almost exclusively of water and was discarded.

After an operating time of 3 hours the installation was already producing 99.5% aniline, and after 23 hours the aniline obtained was 99.8%.

Aniline was obtained at this degree of purity for a further 1000 hours without indications of the commencement of deactivation, whereupon the test was terminated.

The detection limit of the GC analysis used was about 5 ppm.

The byproducts comprised about 16 compounds, which together amounted to about 0.2% of the amount of product.

EXAMPLE 4

30 ml of the catalyst described in Example 2 were introduced into the apparatus described in Example 3 and the installation was operated as described in Example 3.

The catalyst produced a hydrogenation product which was substantially the same as that of the catalyst on the carbon support.

A somewhat improved degree of aniline purity (99.9%) compared with Example 3 was obtained after 24 hours, but after an operating period of 1000 hours the commencement of deactivation was indicated by the presence of about 2 ppm of nitrobenzene in the product.

We claim:
1. A process for producing aromatic amines of formula

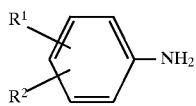

where
R$^1$ and R$^2$ represent hydrogen, methyl or ethyl, independently of each other, and
R$^1$ may in addition represent an amino group,
by the hydrogenation of aromatic nitro compounds of formula

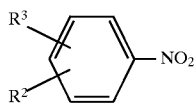

where
R$^2$ and R$^3$ represent hydrogen, methyl or ethyl, independently of each other, and
R$^3$ may in addition represent a nitro group, in the gas phase with H$_2$ on fixed catalysts, characterized in that it is operated at a pressure of 2 to 50 bar and at a temperature in the range 250°–500° C. under adiabatic conditions, wherein a circulating gas flows over the catalyst, which circulating gas contains 3–150 moles of hydrogen, 2–100 moles of aromatic amino groups per mole of nitro groups, and 2–6 moles of water per mole of amino groups, the amount of amine and water formed per unit time is condensed out and the residual circulating gas, optionally after the separation of a purification stream, is recycled, and is enriched with vaporized aromatic nitro compound and with fresh hydrogen.

2. A process according to claim 1, characterized in that aromatic nitro compounds of formula

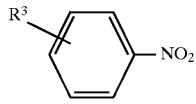

are used, where
R$^3$ represents hydrogen, methyl or ethyl.

3. A process according to claim 1, characterized in that the reaction is conducted in 1–10 reactors connected in series, each reactor of which may be replaced by a maximum of 5 reactors connected in parallel.

4. A process according to claim 3, characterised in that downstream of each reactor the adiabatically accumulated heat of reaction is used for the generation of steam.

5. A process according to claim 3, characterised in that fresh aromatic nitro compound is added to the reaction mixture upstream of each reactor and, independently of this, part of the circulating stream is separated off upstream of the addition of aromatic nitro compound in order to condense out the amine and water formed.

6. A process according to claim 1, characterized in that the penetration depth of the catalyst bed is 1 cm–5 m.

7. A process according to claim 1, characterized in that, per nitro group equivalent, the circulating gas flowing over the catalyst contains 2.5–50 moles of the amino groups to be formed, and independently thereof contains 6 to 125 moles of hydrogen.

8. A process according to claim 1, characterized in that a catalyst containing palladium on α-Al$_2$O$_3$ is used, which contains 1–100 g Pd per liter of α-Al$_2$O$_3$, which is deposited in the form of a skin, wherein the catalyst may additionally contain vanadium and lead and is operated at a maximum temperature of 500° C.

9. A process according to claim 1, characterized in that a catalyst containing palladium on carbon supports is used, the support of which has a BET specific surface of 0.2–10 m$^2$/g, the Pd content of which is 0.001–1.5 weight %, 0–40 relative % of the amount of Pd of which is replaced by one or more metals selected from the group consisting of Rh, Ir and Ru, which catalyst in addition may have a content of 0.1–2 weight %, calculated as sulphur or phosphorus, of a compound containing sulphur or phosphorus wherein all percentages by weight are based on the total weight of the catalyst, and which is operated at a maximum temperature of 480° C.

10. A process according to claim 1, characterized in that the catalyst is loaded with 0.1–20 g of aromatic nitro compound per ml of catalyst per hour.

* * * * *